(12) United States Patent
Qin et al.

(10) Patent No.: US 7,229,689 B2
(45) Date of Patent: Jun. 12, 2007

(54) POLYSACCHARIDE FIBRES

(75) Inventors: Yimin Qin, Northwich (GB); Melanie Rachel Groocock, Stockport (GB)

(73) Assignee: SSL International, Cambridge (GB)

( * ) Notice: Subject to any disclaimer, the term of this patent is extended or adjusted under 35 U.S.C. 154(b) by 365 days.

(21) Appl. No.: 10/415,520

(22) PCT Filed: Nov. 5, 2001

(86) PCT No.: PCT/GB01/04884

§ 371 (c)(1),
(2), (4) Date: Jul. 18, 2003

(87) PCT Pub. No.: WO02/36866

PCT Pub. Date: May 10, 2002

(65) Prior Publication Data

US 2005/0101900 A1    May 12, 2005

(30) Foreign Application Priority Data

Nov. 3, 2000    (GB)    ................................ 0026863.1

(51) Int. Cl.
*D02G 3/00*    (2006.01)
*A61F 13/00*    (2006.01)

(52) U.S. Cl. ...................... 428/372; 428/373; 428/374; 428/393; 428/907; 602/49

(58) Field of Classification Search ................ 428/372, 428/375, 394, 373, 374, 393, 907; 602/49; 424/443, 445, 446, 447, 802, 414, 405
See application file for complete search history.

(56) References Cited

U.S. PATENT DOCUMENTS

| 5,405,644 | A | | 4/1995 | Kato et al. |
| 6,080,420 | A | * | 6/2000 | Qin et al. .................... 424/443 |
| 6,140,257 | A | * | 10/2000 | Kershaw et al. ................ 442/4 |
| 6,458,460 | B1 | * | 10/2002 | Griffiths et al. .......... 428/425.1 |
| 6,471,982 | B1 | * | 10/2002 | Lydon et al. ................ 424/443 |

FOREIGN PATENT DOCUMENTS

JP    09256226    9/1997

* cited by examiner

*Primary Examiner*—Jill Gray
(74) *Attorney, Agent, or Firm*—Duane Morris LLP

(57) ABSTRACT

This invention relates to polysaccharide fibres having water absorption properties characterised by the incorporation within the fibres of at least one substance having antimicrobial properties, and to wound dressings formed from said fibres. The polysaccharide fibres are preferably formed from alginate or alginate containing additional polysaccharide materials to give additional absorbency (such as, for example, sodium carboymethyl cellulose). The fibres preferably contain a silver compound as an antimicrobial agent.

12 Claims, No Drawings

POLYSACCHARIDE FIBRES

The present invention relates to polysaccharide fibres that are useful particularly, but not exclusively, in the manufacture of wound dressings.

Polysaccharides are natural polymers with hydrophilic properties that are particularly useful for the manufacture of wound dressings. In particular, sodium alginate and sodium carboxymethyl cellulose, have been used in the wound dressing industry for manufacturing fibres, gels and hydrocolloid dressings. For example, alginate fibres have been used for the manufacture of Sorbsan™ and Kaltosta™, two of the leading brands in the alginate dressing market. Sodium carboxymethyl cellulose (CMC) is used for making Aquacel™, a hydrofibre wound dressing capable of absorbing wound exudate into the fibre structure, rather than holding the fluid in between fibres.

Fibres made from polysaccharides such as alginate are often used to produce a nonwoven textile structure that has good absorption capacity, as well as the conformity of a textile structure. These fibrous dressings offer an ideal environment for wound healing since on absorbing the wound exudate, the fibres turn into a moist gel by absorbing wound exudate into the structure of the fibre, thereby turning itself into a gel.

Alginate is a natural polysaccharide existing widely in many species of brown seaweeds. Alginate is well known for its ability to form stable gels. On contact with divalent metal ions, typically calcium ions, water soluble alginate solutions typically sodium alginate, reacts with calcium ions and forms a gel. On contact with wound exudates, calcium alginate fibres exchange sodium ions in the wound exudate, wherby the calcium ions in the fibres are replaced by sodium ions in the exudate. As a result, the fibres become a calcium/sodium alginate fibre. Since sodium alginate is water soluble, the fibre absorbs large quantities of exudate and forms a gel in situ on the wound surface.

PCT/GB95/02284 (Advanced Medical Solutions) discloses a method of making fibres by co-spinning alginate with at least one water soluble organic polymeric species. The addition of the water soluble organic polymers makes the dressing more absorbent, thereby extending the duration of the dressing in use.

The present invention is concerned with the provision of anti-microbial properties in polysaccharide fibres.

According to a first aspect of the present invention there is provided polysaccharide fibres having water absorption properties characterised by the incorporation within the fibres of at least one substance having anti-microbial properties.

Preferably, the polysaccharide fibres are made from alginate or alginate containing additional polysaccharide materials to give additional absorbency (particularly sodium carboxymethyl cellulose). Preferably, the fibres are formed by extruding or spinning polysaccharide material from a solution thereof. In particular, in the case of use of alginate and additional polysaccharide material these are preferably co-spun from an aqueous solution into a coagulation bath.

Preferably also, the (or at least one) said antimicrobial substance is a silver compound and in the case of extrusion or spinning as mentioned above, this compound is preferably contained in the said solution. The silver compound(s) may be present in the fibres at concentrations of between 0.1% (w/w) and 2% (w/w), and are preferably present at concentrations of between 0.5% (w/w) and 2% (w/w). Most preferably, the silver compound is able to leach from the fibres. This allows reduction of the bacterial load in a wound to which a dressing comprising fibres of the invention has been applied.

Thus, and in accordance with a particularly preferred embodiment of the present invention, AlphaSan, a silver sodium hydrogen zirconium phosphate (from Milliken Chemical, Spartanburg, USA) is dissolved in an aqueous solution of sodium alginate and sodium carboxymethyl cellulose. AlphaSan is a ceramic, ion exchange resin, containing nominally 3.8% silver, and has proven efficacy against several types of bacteria. The solution can then be extruded via fine holes into a coagulation bath to form fibres. After coagulation of their extruded filament in a calcium chloride bath, the AlphaSan powders can be dispersed in the fibres to give it an anti-microbial effect.

It is known that silver compounds demonstrate good anti-microbial effect. Silver alginate fibres can be made by ion-exchange of a calcium alginate fibre with silver nitrate. However, silver-containing alginate fibres produced in this way tend to have unfavorable physical appearances. The alginate can be oxidised by the silver ions and the fibre turns black, making it unfavorable as a wound dressing material.

With the above mentioned preferred embodiment of the present invention, the silver ions can be bound inside water insoluble particles which are dispersed in the fibre. Oxidation of the fibre by the silver ions need not occur and the fibre can retain its white physical appearance whilst at the same time demonstrating good anti-microbial effect.

Generally, the fibre will comprise a major proportion by weight of alginate, e.g. 30–95%, and a minor proportion of CMC (carboxymethyl cellulose). The alginate can be a grade high in manuronate content such as Manucol DH from Kelco, although alginate high in glucuronate can also be used.

Fibres according to the present invention may be formed into a wound dressing. Any suitable process may be used to form such a wound dressing. Conveniently, however, nonwoven dressings may be formed by carding the fibres to produce a web and then cross lapping the web to form a thick layer of felt, which is then needle punched to form a needled nonwoven structure. The needled felt may then be slit to form individual would dressings.

Thus, and in accordance with a second aspect of the present invention there is provided a wound dressing comprising polysaccharide fibres as hereinbefore defined.

The invention will now be illustrated in the following non-limiting Examples.

EXAMPLE 1

This example describes the production of anti-microbial alginate-CMC fibres, and the formation of a wound dressing therefrom. The fibres comprise 84% Mid-M alginate, 15% CMC and 1% AlphaSan.

A 25 kg batch of fibres was prepared using 0.25 kg AlphaSan, 21 kg alginate and 3.75 kg CMC. These components were mixed in water and extruded via a spinneret plate with 40,000 holes, each having a hole diameter of 70 μm. After being precipitated in a calcium chloride bath, the alginate in the final fibres was in the form of a mixture of calcium and sodium salt (alginate is a polymeric acid with a carboxylic acid group on each monomer unit).

Nonwoven wound dressings were formed from these fibres by carding and needling. Silver was shown to be uniformly distributed in the fibres.

EXAMPLE 2

This example describes physical and performance testing of dressings made from the anti-microbial alginate-CMC fibres of Example 1. The fibres were subjected to a range of different tests, these being as follows.

Wound Model Analysis

The wound model was set up with a flow rate of 1 ml/hour using 0.86% saline solution. A saturated filter paper was placed on the wound model and the dressing was placed on top of this. A 2 kg vented weight was put on top of the dressing and the dressing was left until failure. A time to failure comparison was made between dressings tested on the wound model.

The results were as follows:

| Store weight (g) | End weight (g) | Failure Time (hrs) |
| --- | --- | --- |
| 1.17 | 3.55 | 28.40 |
| 1.09 | 4.08 | 24.00 |

The dressing gelled on contact with fluid and remained gelled throughout the testing of the dressing. The gel was clear/white in colouration and the silver in the dressing did not discolour the dressing in any way. The time to failure on the wound model was good for an alginate dressing.

B.P. Absorbency

The dressings were tested according to the method of the British Pharmocopoeia to see how absorbent they were in saline solution (142 MM Na, 2.5 MM Ca). A piece of 5 cm×5 cm dressing was placed into an extra wide neck polyurethane bottle (Fisher catalogue No. BTK-460-110B), this being a flat bottomed bottle with a sealing lid.

An amount of solution A (as defined in the absorbency test method for alginate wound dressings in the British Pharmcopoeia) 40 times the weight of the dressing was added to the bottle containing the sample of dressing. The lid on the bottle was then sealed and the bottle conditioned in a 36° C. oven for 30 minutes. After this time, the lid was removed from the bottle and the dressing was then lifted from one corner and the solution allowed to drip for 30 seconds.

The dressing was then re-weighed and the amount of fluid absorbed per 1 g of dressing calculated.

The absorbency test was repeated using deionised water and human serum.

The dressing of the invention was found to absorb an average of 20.7 g saline solution/g dressing (n=10); an average of 23.7 g deionised water/g dressing (n=10); and an average of 20.8 g human serum/g dressing (n=2).

Silver Leach Analysis

Silver Leach from the dressing was analysed using the absorbency test method described above, with synthetic exudates being employed as the test solution.

The samples were left for 7 days in a 36° C. incubator and after this time they were lifted from one corner and the solution was allowed to drip for 30 seconds. The solution was analysed for silver content by atomic absorption.

The results using the 1.1 g dressing were as follows:

| Time | Sol A % silver from Dressing | Sol A ppm Delivered from Dressing | Mg of silver delivered from Dressing |
| --- | --- | --- | --- |
| 0 Hours | 0 | 0 | 0 |
| 30 Min | 11.8 | 0.5023 | 0.0221 |
| 2 Days | 9.3 | 0.3955 | 0.0174 |
| 7 Days | 31.0 | 1.3181 | 0.0580 |

| Time | Human Serum % Silver From Dressing | Human Serum ppm Delivered from Dressing | Mg of Silver Delivered from Dressing |
| --- | --- | --- | --- |
| 0 Hours | 0 | 0 | 0 |
| 30 Min | 51.3 | 2.1795 | 0.0959 |
| 2 Days | 64.5 | 2.7409 | 0.1206 |
| 7 Days | 88.0 | 3.7409 | 0.1646 |

MVTR

CEN Method for MVTR

Deionised water was poured into each of the five Paddington cups leaving a gap of 5 mm from the rim of the cup. A circular disc of the material being examined was placed on the centre of the top surface of the chamber ensuring wound contact surface towards the deionised water. The rubber gasket was placed around this and the flange was then clamped in place. The Paddington cups were weighed and the weight recorded. They were then placed into the oven at 37 degrees centigrade with a relative humidity value under 20% for 24 hours. After 24 hours they were removed from the oven and left to cool in a dessicator. They were then reweighed. The MVTR was calculated using the following equation:

$$\frac{(\text{weight 1} - \text{weight 2})}{12.6} \times 10000$$

The results were as follows:

| Start Weight | End Weight | MVTR |
| --- | --- | --- |
| 137.96 | 125.55 | 9849.21 |
| 163.96 | 150.61 | 10595.24 |

Tensile Strength

The dressings were tested for their tensile properties in longitudinal and horizontal direction. They were tested dry in both directions and when wetted with 1 ml of saline and also with 1 ml of deionised water, the wetted dressing being left for 15 seconds to gel before commencing the test. 10 samples were tested for each parameter giving a total of 60 samples tested. The sample size was 2.5 cm width by 10 cm length.

The tensometer was set up with a 10 Newton load cell. The gauge length was set at 50 mm and the crosshead speed was set at 300 mm/min.

The dressings were tested to failure. The tensile elongation [X Head] test method was opened and the following parameters were set.

(Hounsfield Tensometer)
Load Range: 0.1020 Kgf
Extension Range: 500 mm
Speed: 300 mm/min
Sample Length: 50 mm
Preload: 0.0000 Kgf The results obtained were as follows:

| Direction Dressing Tested | Tested Wet or Dry | Average Load | Standard Deviation |
|---|---|---|---|
| Longitudinal | Dry | 0.3551 | 0.0455 |
| Horizontal | Dry | 0.4626 | 0.0664 |
| Longitudinal | Deionised Water | 0.0675 | 0.0194 |
| Horizontal | Deionised Water | 0.1220 | 0.0155 |
| Longitudinal | Saline | 0.1136 | 0.0168 |
| Horizontal | Saline | 0.1827 | 0.0321 |

Weight Per Unit Area

The weight per unit are was calculated as follows:

$$\frac{10000 \times \text{weight}}{\text{area}} = \text{weight per unit area}$$

The weight per unit area was found to be 102.78 gm$^{-2}$.

Sodium Calcium Analysis

A weighed piece of 3" by 3" dressing (w1) was placed into each of three extra wide neck polyethylene bottles (Fisher catalogue number BTK-460-110B). The bottles are flat bottomed with a sealing lid. An amount of solution A (as defined in the absorbency test method for alginate wound dressings in the British Pharmacopoeia) 40 times the weight of the dressing was added to each of the bottles containing the 3" by 3" samples of dressing. The lids on the bottles were then sealed and the bottles conditioned in a 36 degree oven one for 30 minutes, one for 24 hours and finally for 7 days. After this time the lid was removed from the bottle and the dressing was then lifted from one corner and the solution allowed to drip for 60 seconds. The residue solution was then tested for its sodium and calcium contents by atomic absorption.

The results were as follows:

| Time | Na ppm in Solution | Ca ppm in Solution |
|---|---|---|
| 30 Mins | 1719 | 293 |
| 24 Hours | 2117 | 403 |
| 7 Days | 2283 | 463 |

Gel Swelling Properties

The gel swelling properties were assessed by taking the dressing that was lifted from the solution in the sodium calcium analysis test method and recording the weight as (W2).

The wet sample was then centrifuged at 3000 rpm for 10 minutes. The sample was then removed and reweighed (W3).

The centrifuged sample was dried in a 105 degrees centigrade oven overnight before reweighing to give (W4).

From the information gained the amount of fluid held in the fibres could be calculated and also the weight of the fluid held between the fibres could be calculated.

W2–W3 is the weight of fluid held between the fibres.
W3–W4 is the weight of fluid held inside the fibres.

The results were as follows:

| Duration | Measurement | Wt in Grams |
|---|---|---|
| 30 Mins | Wt of Fluid Between Fibres | 9.3152 |
| 4 Hours | Wt of Fluid Between Fibres | 9.7115 |
| 24 hours | Wt of Fluid Between Fibres | 11.0955 |
| 7 Days | Wt of Fluid Between Fibres | 12.8623 |
| 30 Mins | Wt of Fluid Held inside Fibres | 1.9951 |
| 4 Hours | Wt of Fluid Held inside Fibres | 1.9939 |
| 24 hours | Wt of Fluid Held inside Fibres | 2.0313 |
| 7 Days | Wt of Fluid Held inside Fibres | 2.0740 |

Acidity/Alkalinity Testing 3 g of dressing being examined was weighed out. To this 30 ml of sodium chloride and calcium chloride solution was added. (142 MM Na, 2.5 MM Ca). This was left to stand for 2 hours. After 2 hours the solution was decanted. To 5 ml of the decanted solution 0.05 ml of Phenol Red solution was added. The volume of 0.01 M Sodium Hydroxide VS required to change the colour of the solution was determined. This volume was the subtracted from the volume of Sodium Hydroxide VS required to change the colour of the solution prepared in the same manner but without the material being examined. The difference should not be more than 1.0 ml to pass the B.P. Specification.

The pH was 6.65 and the acidity/alkalinity was 0.02, this being within the accepted limits according to the B.P. Specification.

EXAMPLE 3

This example describes the testing of the antimicrobial properties of the fibres of Example 2 in the form of a wound dressing, as compared to three commercially available wound dressings comprising non-silver-containing fibres.

The wound dressings were tested dressings using a direct inoculation method. The test method was designed to determine the reduction in the number of bacteria for each of the alginate wound dressings. Testing involved inoculating samples of the alginate wound dressings with a range of bacteria, then determining the change in bioburden over a 3-day period.

The anti-microbial activity of the wound dressings was tested against 10 different bacteria, these being *S. aureus* (NCIMB 9518), *S. aureus* (NCTC 13142), *S. aureus* (NCTC 13143), *Pseudomonas aeruginosa* (NCIMB 8626), *Escherichia coli* (NCIMB 8545), *Proteus vulgaris* (NCIMB 4175), *Enterococcus faecalis* (NCIMB 13280), *Staphylococcus epidermidis* (NCIMB 12721), *Steptococcus pyrogenes* (NCIMB 8884), and *Bacillus subtilis* (NCIMB 8054).

The bacteria were grown in sterile Tryptone soya broth for 18–24 hours at 35° C., and then subcultured onto Tryptone soya agar at 35° C. for 18–24 hours. A suspension of bacteria containing approximately 1×10$^8$ colony forming units per ml (cfu/ml) was prepared in 10 ml phosphate buffered saline (PBS) using a Neubauer counter. The suspension was then diluted by adding 0.67 mls 1 to 100 mls PBS to prove a working suspension containing $6.67 \times 10^5$ cfu/ml. Two 2 cm×2 cm pieces of wound dressing were placed in each of seven petri dishes. 1.5 ml of the $6.67 \times 10^5$ cfu/ml bacterial suspension was pipetted onto each sample (equivalent of $1 \times 10^6$ cfu/dressing), the sample was turned over using sterile forceps, and the timer started. At 0 hours, one piece of wound dressing was removed from a petri dish and placed in a stomacher bag. 50 ml of neutraliser was added and the sample stomached for 30 seconds to extract the bacteria ($10^{-2}$ dilution). 100 μl of the extract from 1.4 was then pipetted into 10 ml neutraliser and mixed ($10^{-4}$ dilution). 0.5 ml of the $10^{-4}$ dilution was pipetted into each of two labelled petri dishes. Molten TSA was added to the dishes, mixed and allowed to set.

A second piece of inoculated wound dressing was also tested in this manner.

Further duplicate pieces of inoculated wound dressing were tested after 3, 6, 9, 24, 48 and 72 hours, testing both the $10^{-2}$ and $10^{-4}$ dilutions. After initial inoculation, all 3, 6, 9, 24, 48 and 72 hours samples were placed and sealed in bags and incubated at 35° C.

Plates were incubated for 3 days at 35° C. then colonies counted.

The results are shown below, "Test Sample" referring to the wound dressing of the present invention, and Comparative Examples 1 to 3 being non-silver containing alginate dressings.

TABLE 1

Direct Inoculation of Dressings using 1.5 ml *S. aureus* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 66.735 | 46.115 | 74.649 | 79.679 |
| 6 hour | 45.932 | 23.814 | 56.203 | 62.656 |
| 9 hour | 23.996 | 7.971 | 42.503 | 58.645 |
| 24 hour | $<1.03 \times 10^{-3}$ | $<1.01 \times 10^{-3}$ | 0.548004 | 0.11854 |
| 48 hour | $<1.03 \times 10^{-3}$ | $<1.01 \times 10^{-3}$ | $<1.80 \times 10^{-3}$ | $<8.91 \times 10^{-4}$ |
| 72 hour | $<1.03 \times 10^{-3}$ | $<1.01 \times 10^{-3}$ | $<1.80 \times 10^{-3}$ | $<8.91 \times 10^{-4}$ |

TABLE 2

Direct Inoculation of Dressings using 1.5 ml MRSA 13142 Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 0.804386 | 9.642 | 124.1551 | 76.052 |
| 6 hour | $<8.80 \times 10^{-6}$ | 1.089 | 63.519 | 91.760 |
| 9 hour | $<8.80 \times 10^{-6}$ | Not measured | 50.298 | 59.828 |
| 24 hour | $<8.80 \times 10^{-6}$ | $<7.70 \times 10^{-6}$ | 0.0964 | $<8.60 \times 10^{-6}$ |
| 48 hour | $<8.80 \times 10^{-6}$ | $<7.70 \times 10^{-6}$ | $<9.90 \times 10^{-6}$ | $<8.60 \times 10^{-6}$ |
| 72 hour | $<8.80 \times 10^{-6}$ | $<7.70 \times 10^{-6}$ | $<9.90 \times 10^{-6}$ | $<8.60 \times 10^{-6}$ |

TABLE 3

Direct Inoculation of Dressings using 1.5 ml MRSA 13143 Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 36.044 | 51.927 | 84.346 | 135.2697 |
| 6 hour | 7.688 | 18.661 | 71.087 | 120.125 |
| 9 hour | 0.466 | 5.071 | 48.987 | 71.784 |
| 24 hour | $<1.85 \times 10^{-5}$ | $<2.03 \times 10^{-5}$ | 2.8655 | 0.01558 |
| 48 hour | $<1.85 \times 10^{-5}$ | $<2.03 \times 10^{-5}$ | $<1.84 \times 10^{-5}$ | $2.07 \times 10^{-5}$ |
| 72 hour | $<1.85 \times 10^{-5}$ | $<2.03 \times 10^{-5}$ | $<1.84 \times 10^{-5}$ | $2.07 \times 10^{-5}$ |

TABLE 4

Direct Inoculation of Dressings using 1.5 ml *Ps. aeruginosa* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 0.00977 | 1.4085 | 49.0018 | 85.1562 |
| 6 hour | $<3.25 \times 10^{-5}$ | 0.3521 | 9.9819 | 259.1146 |
| 9 hour | $<3.25 \times 10^{-5}$ | 55.11 | 1.4519 | >520.8333 |
| 24 hour | $<3.25 \times 10^{-5}$ | >352.11 | 0.0526 | >520.8333 |
| 48 hour | $<3.25 \times 10^{-5}$ | >352.11 | 33.9382 | >52083.33 |
| 72 hour | $<3.25 \times 10^{-5}$ | >352.11 | 362.9764 | >52083.33 |

TABLE 5

Direct Inoculation of Dressings using 1.5 ml *E. coli* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 0.004597 | 58.77193 | 114.9669 | 82.42812 |
| 6 hour | $<1.79 \times 10^{-5}$ | 19.73684 | 70.33113 | 82.42812 |
| 9 hour | $<1.79 \times 10^{-5}$ | 12.5 | 52.5828 | 78.48775 |
| 24 hour | $<1.79 \times 10^{-5}$ | $<2.19 \times 10^{-5}$ | 51.3907 | 92.43876 |
| 48 hour | $<1.79 \times 10^{-5}$ | $<2.19 \times 10^{-5}$ | 133.1126 | 212.9925 |
| 72 hour | $<1.79 \times 10^{-5}$ | $<2.19 \times 10^{-5}$ | 4.2384 | 21299.25 |

TABLE 6

Direct Inoculation of Dressings using 1.5 ml *S. pyrogenes* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | $<1.39 \times 10^{-4}$ | 13.33333 | 96.61017 | 11.4035 |
| 6 hour | $<1.39 \times 10^{-4}$ | Not measured | Not measured | Not measured |
| 9 hour | $<1.39 \times 10^{-4}$ | Not measured | Not measured | Not measured |
| 24 hour | $<1.39 \times 10^{-4}$ | $<9.52 \times 10^{-3}$ | $<1.69 \times 10^{-2}$ | $<8.77 \times 10^{-3}$ |
| 48 hour | $<1.39 \times 10^{-4}$ | $<9.52 \times 10^{-3}$ | $<1.69 \times 10^{-2}$ | $<8.77 \times 10^{-3}$ |
| 72 hour | $<1.39 \times 10^{-4}$ | $<9.52 \times 10^{-3}$ | $<1.69 \times 10^{-2}$ | $<8.77 \times 10^{-3}$ |

TABLE 7

Direct Inoculation of Dressings using 1.5 ml *P. vulgaris* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 3.9519 | 4.264099 | 72.20267 | 44.05091 |
| 6 hour | 1.9473 | 1.5130667 | 57.35398 | 16.3254 |
| 9 hour | 0.5029 | 0.137552 | 41.8719 | 11.28943 |
| 24 hour | $<5.72 \times 10^{-6}$ | 0.18157 | 23.29346 | 8.35639 |
| 48 hour | $<5.72 \times 10^{-6}$ | 0.01169 | 5.70021 | 5.70021 |
| 72 hour | $<1.03 \times 10^{-6}$ | $<6.88 \times 10^{-6}$ | 1.078114 | 1.078114 |

TABLE 8

Direct Inoculation of Dressings using 1.5 ml *S. epidermidis* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 12.6990 | 11.66474 | 15.2846 | 67.76233 |
| 6 hour | 11.2206 | 6.33449 | 10.6504 | 43.10999 |
| 9 hour | 6.06520 | 3.05137 | 6.78861 | 29.70923 |
| 24 hour | $<3.79 \times 10^{-6}$ | $<3.86 \times 10^{-6}$ | 0.258943 | 0.439949 |
| 48 hour | $<3.79 \times 10^{-6}$ | $<3.86 \times 10^{-6}$ | $<4.07 \times 10^{-6}$ | $<1.26 \times 10^{-5}$ |
| 72 hour | $<3.79 \times 10^{-6}$ | $<3.86 \times 10^{-6}$ | $<4.07 \times 10^{-6}$ | $<1.26 \times 10^{-5}$ |

TABLE 9

Direct Inoculation of Dressings using 1.5 ml *E. faecalis* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 63.07692 | 56.90608 | 120.77012 | 110.23256 |
| 6 hour | 44.61538 | 21.54696 | 109.10151 | 90.23255 |
| 9 hour | 40 | 23.75691 | 107.35122 | 117.2093 |
| 24 hour | 5.507692 | 0.071823 | 121.35355 | 52.13270 |
| 48 hour | $1.02 \times 10^{-4}$ | $<5.52 \times 10^{-5}$ | 76.42940 | 0.260465 |
| 72 hour | $<5.13 \times 10^{-5}$ | $<5.52 \times 10^{-5}$ | 60.09335 | $4.65 \times 10^{-5}$ |

TABLE 10

Direct Inoculation of Dressings using 1.5 ml *B. subtilis* Inoculum (Phosphate Buffered Saline)

| | Percentage Recovery | | | |
|---|---|---|---|---|
| Time Interval | Test Sample | Comparative Example 1 | Comparative Example 2 | Comparative Example 3 |
| 0 hour | 100 | 100 | 100 | 100 |
| 3 hour | 37.168142 | 23.40426 | 14.61794 | 37.3563 |
| 6 hour | 23.00885 | 20.21277 | 14.61794 | 27.0115 |
| 9 hour | 33.628319 | 22.87234 | 14.28571 | 41.954 |
| 24 hour | 18.106195 | 31.91489 | 18.27243 | 31.6092 |
| 48 hour | 35.840708 | 28.7234 | 22.92359 | 39.6552 |
| 72 hour | 42.477876 | 45.12766 | 12.62458 | 174.138 |

All samples were tested against the ten bacteria described above, including two strains of MRSA (*S. aureus* NCTC 13142 (EMRSA 15) and *S. aureus* NCTC 13143 (EMRSA 16). Results show for the Test Sample no EMRSA 15 were detectable after 6 hours, for Comparative Example 1 and Comparative Example 3 this was not the case until 24 hours and Comparative Example 2 not until 48 hours. For no colonies of EMRSA 16 to be detected in the Test Sample the time increased to 24 hours, this was also the case for Comparative Example 1 but for both Comparative Example 2 and Comparative Example 3 48 hours were required for no EMRSA 16 to be detected. The results for non-methicillin resistant *S. aureus* (NCIMB 9518), a mirrored the results obtained for EMRSA 16.

The results for *P. aeruginosa* showed the Test Sample to be much more active against *P. aeruginosa* than the other three competitor dressings. Only a few *P. aeruginosa* colonies were detected after 3 hours for Test Sample, for the three competitor dressing colonies were still detectable at 72 hours. The results show that for both Comparative Example 1 and Comparative Example 2 the numbers present in the dressing begin to fall but at 6 hours and 24 hours respectively the trend reversed and the numbers started to increase, and by 72 hours the number of microorganisms present increased to a level greater than the original inoculum. The initial fall seen for Comparative Example 1 and Comparative Example 2 is not seen in the results for Comparative Example 3, these data showing that Comparative Example 3 has very little antimicrobial effect and the numbers have increased significantly when compared to the initial inoculum.

The results for *E. coli* showed no *E. coli* detected after 6 hrs for the Test Sample, after 24 hours for Comparative Example 1 and for Comparative Example 2 and Comparative Example 3 *E. coli* colonies were still detectable after 72 hours and for Comparative Example 3, as with the *P. aeruginosa* results, a clear increase was noted when compared to the inoculum.

The results for *S. pyrogenes* (NCIMB 8884) shown in Table 6 showed for Test Sample no *Streptococcus* remained after 3 hours. For the three competitor dressings no result is recorded at 6/9 hours. This is due to the fact that the dilution plated ($10^{-4}$) was not low enough to detect any remaining microorganisms. The most accurate result that can be obtained is that $<2.5 \times 10^3$ cfu/ml of *S. pyrogenes* remained at 6 hours, however there is still the possibility that no organisms remained at 6 hours.

The results for *Proteus vulgaris* (NCIMB 4175) documented in table 7 shows no *P. vulgaris* colonies detectable after 48 hours for Test Sample. The Test Sample showed the best activity against *P. vulgaris* as it still detectable in Comparative Example 1 at 48 hours and at 72 hours for Comparative Example 2 and Comparative Example 3.

Test Sample and Comparative Example 1 show similar activity against *S. epidermidis* NCIMB 12721 (results in Table 8) with no colonies detectable at 24 hours, Comparative Example 2 and Comparative Example 3 prove to be less effective as colonies are still present at 24 hours, however no colonies were detected at 48 hours.

Test Sample proved to be less effective against *E. faecalis* than many of the other organisms, only after 72 hours were colonies not detectable; this was also the case for Comparative Example 3. Comparative Example 1 proved to be more effective than Test Sample against *E. faecalis* as no colonies were detectable at 48 hours. Comparative Example 2 appeared to be the least effective with greater than 60% of the original inoculum still remaining at 72 hours.

*Bacillus subtilis* proved to be the least susceptible of all, the organisms tested to all the dressings, however Comparative Example 2 proved to have the greatest antimicrobial effect with only 12% of the original inoculum remain at 72 hour. For Test Sample and Comparative Example 1 approximately 45% of the original inoculum remained at 72 hours and for Comparative Example 3 a clear increase was seen.

Generally Test Sample performed better than or equally as well as the Comparative Example 1 dressing for all the microorganisms tested and both showed a greater antimicrobial effect than both Comparative Example 2 and Comparative Example 3 with the exception of Comparative Example 2 against *B. subtilis*. The Test Sample showed the greatest antimicrobial effect against EMRSA 15, *P. aeruginosa* and *E. coli*.

The invention is not intended to be restricted by details of the above Examples which are described by way of illustration only.

The invention claimed is:

1. Polysaccharide fibres having water absorption properties and anti-microbial properties, said fibres comprise cospun alginate and carboxymethyl cellulose having anti-microbial particles dispersed therein, wherein said particles are silver sodium hydrogen zirconium phosphate, and wherein said particles are present in a concentration of between 0.1% (w/w) and 2% (w/w).

2. Polysaccharide fibres according to claim 1, wherein the fibres comprise a major proportion by weight of alginate of between 30% and 95% inclusive.

3. Polysaccharide fibres according to claim 1, wherein the silver sodium hydrogen zirconium phosphate is present in the fibres at a concentration of between 0.5% (w/w) and 2% (w/w).

4. Polysaccharide fibres according to claim 1, wherein said alginate is high in manuronate content.

5. Polysaccharide fibres according to claim 1, wherein said alginate is high in glucuronate content.

6. A wound dressing comprising polysaccharide fibres according to claim 1.

7. A wound dressing according to claim 6, wherein the wound dressing is a nonwoven felt dressing.

8. A wound dressing according to claim 7, wherein said wound dressing is formed by:
    (a) carding said polysaccharide fibres to produce a web;
    (b) cross lapping said web to form a thick layer of felt;
    (c) needle punching said thick layer of felt to form a needled non-woven structure; and,
    (d) slitting said needled non-woven structure to form individual wound dressings.

9. Polysaccharide fibres having water absorption properties and anti-microbial properties, said fibres comprise coextruded alginate and carboxymethyl cellulose having anti-microbial particles dispersed therein, wherein said particles are silver sodium hydrogen zirconium phosphate, and wherein said particles are present in a concentration of between 0.1% (w/w) and 2% (w/w).

10. A wound dressing comprising polysaccharide fibres according to claim 9.

11. A wound dressing according to claim 10, wherein the wound dressing is a nonwoven felt dressing.

12. A wound dressing according to claim 11, wherein said wound dressing is formed by:
    (a) carding said polysaccharide fibres to produce a web;
    (b) cross lapping said web to form a thick layer of felt;
    (c) needle punching said thick layer of felt to form a needled non-woven structure; and,
    (d) slitting said needled non-woven structure to form individual wound dressings.

* * * * *

UNITED STATES PATENT AND TRADEMARK OFFICE
CERTIFICATE OF CORRECTION

| | | |
|---|---|---|
| PATENT NO. | : 7,229,689 B2 | Page 1 of 1 |
| APPLICATION NO. | : 10/415520 | |
| DATED | : June 12, 2007 | |
| INVENTOR(S) | : Yimin Qin and Melanie Rachel Groocock | |

It is certified that error appears in the above-identified patent and that said Letters Patent is hereby corrected as shown below:

Title Page

[73]: Change "SSL International, Cambridge (GB)" to read --Medlock Medical Limited, Oldham, United Kingdom--.

Signed and Sealed this

Twenty-sixth Day of April, 2011

David J. Kappos
*Director of the United States Patent and Trademark Office*